(12) United States Patent
Hoffmann et al.

(10) Patent No.: US 9,874,480 B2
(45) Date of Patent: *Jan. 23, 2018

(54) CHARACTERIZING CONTENTS OF CONDUITS, IN PARTICULAR MULTIPHASE FLOW CONDUITS

(75) Inventors: Rainer Josef Hoffmann, Unterhaching (DE); William George Clark, Porsgrunn (NO); Lene Amundsen, Porsgrunn (NO); Ruben Schulkes, Sandefjord (NO)

(73) Assignee: STATOIL PETROLEUM AS, Stavanger (NO)

( * ) Notice: Subject to any disclaimer, the term of this patent is extended or adjusted under 35 U.S.C. 154(b) by 388 days.

This patent is subject to a terminal disclaimer.

(21) Appl. No.: 14/375,404

(22) PCT Filed: Jan. 30, 2012

(86) PCT No.: PCT/EP2012/051432
§ 371 (c)(1),
(2), (4) Date: Oct. 1, 2014

(87) PCT Pub. No.: WO2013/113356
PCT Pub. Date: Aug. 8, 2013

(65) Prior Publication Data
US 2015/0020580 A1    Jan. 22, 2015

(51) Int. Cl.
*G01K 13/02* (2006.01)
*G01N 25/18* (2006.01)
(Continued)

(52) U.S. Cl.
CPC .............. *G01K 13/02* (2013.01); *G01F 1/74* (2013.01); *G01K 1/026* (2013.01); *G01N 25/18* (2013.01); *G01K 2013/026* (2013.01)

(58) Field of Classification Search
CPC ........................................................ G01K 13/02
(Continued)

(56) References Cited

U.S. PATENT DOCUMENTS 5,526,696 A    6/1996  Cappi
5,980,102 A *  11/1999  Stulen .................... G01N 25/18
                                                        374/138
(Continued)

FOREIGN PATENT DOCUMENTS

GB      2470941 A        12/2010
WO      WO 2010142999 A2 * 12/2010 ........... G01F 1/6847

OTHER PUBLICATIONS

M. Lashkarbolooki et al: "Experimental Investigation of Wax Deposition in Kermanshah Crude Oil throught a Monitored Flow Loop Apparatus", Energy & Fuels, vol. 24, No. 2, Feb. 18, 2010, XP55019934, pp. 1234-1241.

*Primary Examiner* — Laura Martin
*Assistant Examiner* — Jean Morello
(74) *Attorney, Agent, or Firm* — Birch, Stewart, Kolasch & Birch, LLP

(57) ABSTRACT

A method and apparatus for determining contents of a conduit containing at least one fluid is described. The conduit may be at least partially defined by at least one wall portion. The wall portion may be cooled. After cooling said, the temperature at least one temperature sensor located adjacent to the wall portion may be measured. A characteristic of said contents is determined based on said measured temperature at the or each temperature sensor.

24 Claims, 8 Drawing Sheets

(51) Int. Cl.
*G01F 1/74* (2006.01)
*G01K 1/02* (2006.01)

(58) Field of Classification Search
USPC .......................................... 73/61.44, 204.11
See application file for complete search history.

(56) References Cited

U.S. PATENT DOCUMENTS

| | | | |
|---|---|---|---|
| 7,842,508 B2 | 11/2010 | Palermo et al. | |
| 2007/0006640 A1* | 1/2007 | Gysling | G01F 1/36 73/61.44 |
| 2008/0163692 A1 | 7/2008 | Huang et al. | |
| 2010/0258265 A1* | 10/2010 | Karanikas | E21B 43/243 165/45 |
| 2014/0216152 A1* | 8/2014 | Schuller | G01F 1/6847 73/204.11 |

* cited by examiner

CHARACTERIZING CONTENTS OF CONDUITS, IN PARTICULAR MULTIPHASE FLOW CONDUITS

TECHNICAL FIELD

The invention relates to the field of determining contents of conduits. In particular embodiments, the invention relates to determining a characteristic of contents of a conduit containing a fluid from a multiphase flow from a well.

BACKGROUND

Fluids may be conveyed using conduits, conveniently as a multiphase flow, in which more than one fluid is present at the same time. In oil and gas production, fluids from a well may be conveyed in a multiphase flow. This is advantageous because where more than one fluid is to be transported only one pipeline is needed. This is particularly advantageous in environments that are difficult to reach, such as sea beds and harsh climates, as the use of only one pipeline greatly reduces capital costs. Further downstream, the multiphase flow is received through a separator which separates the fluids of the multiphase flow before they are carried onward for further processing into a petroleum product.

The different fluids of a multiphase flow have different flow characteristics governed by their differing viscosities and densities. This makes it difficult to characterize multiphase flow. It is important to be able to characterize this as the flow characteristics describe the flow conditions. In turn, this is important for process control. For example, in pipe equipment one may wish to avoid excessive liquid accumulation. In separator equipment, one may wish to avoid contamination of the separator output (e.g. water into oil or oil into water). The flow characteristics may also indicate whether plugging of the flow or corrosion and erosion of pipeline and other equipment is likely. Plugging can occur by the formation of waxy deposits inside a pipeline or separator. In order to convey fluids in a multiphase flow safely, and with proper control, it is therefore imperative to have a good knowledge about the flow characteristics. One of the more important flow characteristics is the phase distribution (sometimes termed flow regime).

Flow characteristics are typically determined using empirical equations that have been tested using laboratory experiments. However, these equations are limited as they cannot take account of all of the variables that may be present in a working multiphase flow system, such as inclination of equipment, variations in flow rate and so on. Furthermore, as the test rigs used to verify the empirical equations have significantly smaller diameters than the equipment actually used in production, the validity of the models for the full scale production equipment is unknown.

Multiphase flow can also be predicted theoretically using models and equations but these suffer similar limitations to using empirical models.

Other techniques for determining flow characteristics involve using flow rates or using heat sources and associated probes.

SUMMARY

The inventors have realised that there are drawbacks with using empirical equations to estimate flow characteristics. Flow rate techniques may be inaccurate or invasive and therefore expensive and disruptive. In addition, it is realised that there can be drawbacks with applying heat to equipment, in particular where such equipment may have temperature tolerance limitations.

According to a first aspect there is provided a method of determining contents of a conduit containing at least one fluid. The conduit is at least partially defined by at least one wall portion. The wall portion is cooled. After said wall portion is cooled, the temperature is measured at at least one temperature sensor located adjacent to the wall portion. A characteristic of the contents of the conduit is determined based on said measured temperature at the or each temperature sensor.

The first aspect may optionally include in any appropriate combination and in relation to any aspect further features or steps as defined in the claims appended hereto.

According to a second aspect, there is provided apparatus for determining contents of a conduit containing at least one fluid. The conduit is at least partially defined by at least one wall portion. The apparatus is provided with at least one temperature sensor adapted to be fitted adjacent to the wall portion and cooling means for cooling said wall portion. A processor is provided for measuring the temperature from the or each temperature sensor. The processor is adapted to determine a characteristic of said contents based on said measured temperature from the or each temperature sensor.

The second aspect may optionally include further features, in any appropriate combination and in relation to any aspect, as defined in the claims appended hereto.

According to a third aspect, there is provided a computer device for determining contents of a conduit containing at least one fluid. The conduit is at least partially defined by at least one wall portion. The computer device comprises an in/out device for receiving, from at least one temperature sensor adjacent to the wall portion, data indicative of a temperature of the contents of the conduit in proximity to the or each temperature sensor in response to cooling of the wall portion. The computer device also has a processor arranged to determine a characteristic of the contents based on the measured temperature at the or each temperature sensor.

The third aspect may include further features in any appropriate combination and in relation to any aspect, as defined in the claims appended hereto.

According to a fourth aspect, there is provided a computer program, comprising computer readable code which, when run on a computer device, causes the computer device to behave as a computer device as described above in the third aspect.

According to a fifth aspect, there is provided a computer program product comprising a computer readable medium and a computer program as described above in the fourth aspect, wherein the computer program is stored on the computer readable medium.

DETAILED DESCRIPTION

Figure 1:
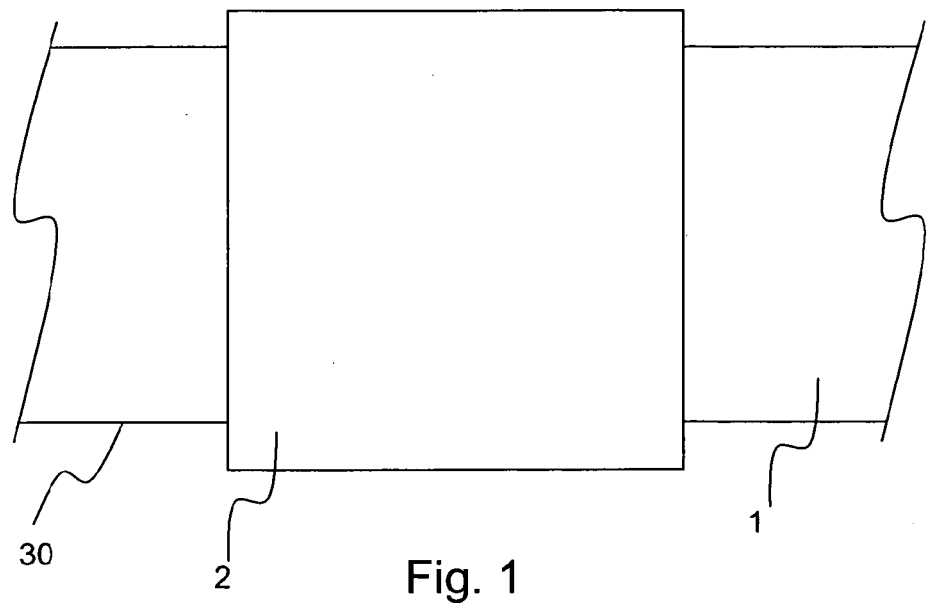
FIG. 1 is a side view of a separator and cooling chamber according to an embodiment of the invention.

Referring to FIG. 1, there is illustrated production equipment 1 with a cooling chamber 2 arranged adjacent to a wall of the production equipment 1. The production equipment 1 in this example is a tubular separator, although the cooling chamber 2 may be used with any type of production equipment, e.g. disposed around or adjacent to a wall thereof. The cooling chamber is arranged to receive a fluid therethrough for cooling the production equipment, or part thereof. The cooling chamber can take different forms. It will be appreciated that the chamber could be a channel, duct or annular space providing a fluid adjacent to a surface, for example an outer surface of the wall, of the production equipment 1.

Figure 2:
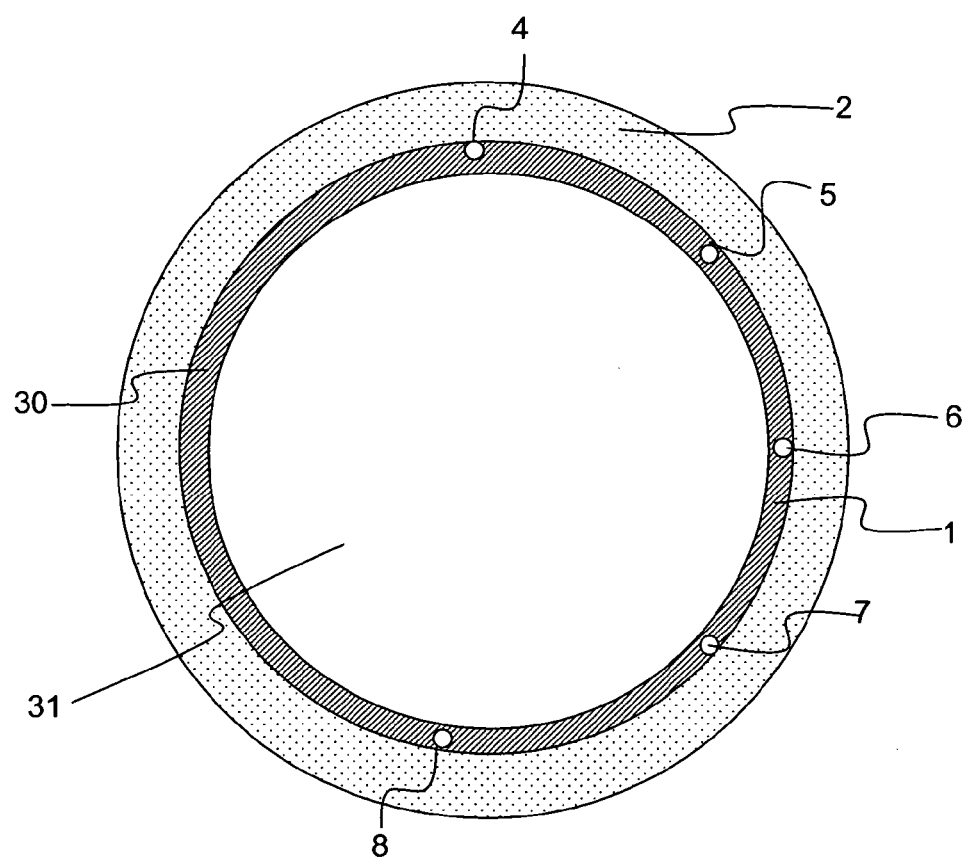
FIG. 2 is an end on cross-sectional view of the separator according to an embodiment of the invention.

Referring to FIG. 2, the internal arrangement of the cooling chamber 2 and production equipment 1 can be seen in more detail. The production equipment 1 has a conduit 31 defined therein for receiving a multiphase flow. The conduit 31 is provided inside of the wall, and is defined by an inner wall surface, whilst the cooling chamber 2 is provided around an outside of the wall 31. It can be seen that a plurality of temperature sensors 4, 5, 6, 7, 8 are also disposed around the production equipment 1. To ensure good contact between the temperature sensors and the wall 30 of the production equipment 1, grooves may be introduced to an outer surface of the wall. Each groove is used to house a temperature sensor.

Figure 3:
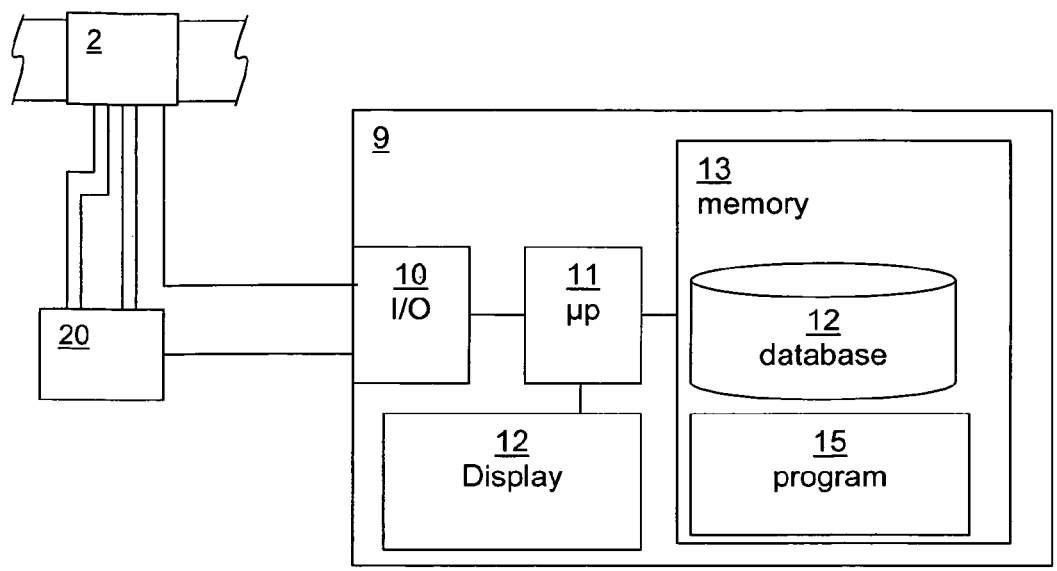
FIG. 3 illustrates schematically in a block diagram a system for characterizing multiflow regimes according to an embodiment of the invention.

Referring to FIG. 3, there is illustrated a system for characterizing multiphase flow. As can be seen, the cooling chamber 2 is connected to a fluid supply apparatus 20 used for providing a flow of cold fluid, for cooling the production equipment, through the cooling chamber. The fluid supply apparatus 20 may also be used to supply a purge gas to the cooling chamber to replace the cold fluid. The fluid supply apparatus may be connected to a fluid source and may include controllable valves used to stop, start and/or control the flow of cold fluid, and optionally the purge gas, from a respective source into and out of the cooling chamber 2.

The temperature sensors are connected to a computer device 9 using an In/Out device 10. The In/Out device 10 is used for sending instructions to and for receiving data from the temperature sensors. The processor 11 is also used for analyzing measurements taken from the temperature sensors. It will be appreciated that these functions may be implemented using different processors, but for the sake of clarity only one processor 11 is shown.

Similarly, the fluid supply apparatus is connected to the computer device 9 using the In/Out device 10. The In/Out device 10 is used for sending instructions to the fluid supply apparatus 20, for example to control a flow valve, and for receiving data therefrom, for example to provide valve status information or the like. A processor 11 is used for generating instructions to be sent to the fluid supply apparatus 20 to control the flow of cold fluid through the chamber and cooling of the production equipment.

In this exemplary embodiment, a display 12 is also provided for allowing a user to see the results of the analysis of information from the temperature sensors. A computer readable medium in the form of a memory 13 is also provided. The memory 13 can be used for storing collected data, pre-programmed instructions for the fluid supply apparatus 20 and temperature sensors, and a database 14 of thermal responses and Prandtl numbers for a variety of fluids and fluid mixtures under different conditions. The memory 13 may also be used to store a program 15 that includes instructions to be executed by the processor.

Note that FIG. 3 illustrates a controller in the form of a computer device 9 connected to a single item of production equipment 1. It will be appreciated that a single computer device 9 may be connected to a plurality of items of production equipment, or to control a plurality of cooling chambers disposed at different points on one or more items of production equipment in order to characterize multiphase flow in different items of production equipment or at different points on the same production equipment.

When the production equipment 1 contains a multiphase fluid, and it is required to in some way characterize the flow of the multiphase fluid, the processor 11 sends an instruction to the fluid supply apparatus 20 to provide a short pulse of cold fluid to the wall of the production equipment by providing the cooling chamber 2 with a cold fluid for a short period of time. The time is selected to ensure that a reasonable temperature response can be obtained, which is based on the cooling effect provided by the cooling chamber and supply apparatus. When the cooling chamber 2 receives a cold fluid, it begins to cool down and so cools the wall of the production equipment 1. Heat from fluids inside the production equipment is conducted through the wall and heats up the fluid contained within the cooling chamber 2. The fluid in this example comprises output from a subsurface well.

When the supply of the cooling chamber 2 with cold fluid is stopped, the temperature of the walls of the production equipment 1 starts to rise as the heat from the fluid contained within the production equipment 1 is dissipated into the fluid contained within the cooling chamber 2. The rate at which the temperature rises is dependent, among other things, upon the nature of the fluid adjacent to the wall of the production equipment 1, and in particular on the heat transfer coefficient between the inner wall of the production equipment 1 and the fluid adjacent to the inner wall surface. If the wall has a waxy layer deposited on its inside surface, this also affects the heat transfer coefficient between the wall and the fluid adjacent to the wall.

The temperature of the walls is measured using the temperature sensors. The measurement signal of particular interest is the transient temperature response after the flow of cold fluid is stopped. The measurement time for one cold fluid pulse is determined by the thermal mass that needs to be warmed up. With reference to FIG. 2, this includes the separator pipe wall (with any deposit), the fluid in the annulus defined by the chamber, and the outer wall of the chamber 2. The wall of the production equipment and the chamber wall may be formed from a metal such as steel.

The measurement time can be optimised by changing the thermal mass. For example, reducing the thermal mass reduces the measurement time. One way to reduce the thermal mass is to first flood the chamber 2 with a cold liquid such as cold water until the separator wall has reached a stable cold temperature (i.e. by applying a pulse of cold water). Once a stable temperature is reached, a pressurized purge gas, such as air or nitrogen or the like, is supplied to the chamber and used to quickly flush out all of the water from the chamber, such that only gas is present during the measurement period. The thermal mass is reduced as it is effectively only the separator wall that is warmed up, since the gas in the annulus has almost no heat capacity. Pulses of cold fluid can then be applied and measurements of the temperature response made more frequently.

A further benefit of gas-flushing is that liquid convection inside the chamber is avoided: If liquid is kept in the annulus during the measurement process and different regions are warmed up at different rates depending upon the location around the separator, this might lead to variations in temperature of the liquid contained in the chamber. This in turn, would start convection in the liquid which can disturb the measurement process. The gas flushing process may therefore help to improve the measurability and quality of measurement of the thermal response.

By subjecting the wall of the production equipment to cooling by a pulse of cold fluid, the multiphase flow inside the equipment will also experience some cooling, at least temporarily, which may give rise to a deposit of wax on an inside surface of the production equipment or wall of the conduit, near the cooling chamber. Such a wax deposit affects heat transfer behaviour. From time to time therefore, it may be desirable that the cooling chamber also be flushed with a hot fluid to release wax build-ups. The supply of the hot fluid can be performed and controlled using the fluid supply apparatus and the computer device, in a similar manner to the supply of a cold fluid, and purge gas as explained above.

The heat transfer coefficient depends on the Prandtl, $P_r$, number, which reflects the fluid's thermal properties. The Prandtl numbers for typically transported fluids (oil, gas, water) differ enough to show a significant difference in the measured thermal response.

The Prandtl number is dimensionless, as it is a ratio of momentum diffusivity to thermal diffusivity, and can be defined by:

$$P_r = \frac{v}{\alpha} = \frac{c_p \mu}{k} \quad (1)$$

where v is kinematic viscosity, $\alpha$ is thermal diffusivity, $\mu$ is dynamic viscosity, k is thermal conductivity, $c_p$ is specific heat, and $\rho$ is density. A low $P_r$ usually indicates that conductive transfer is a dominant mechanism of heat transfer, and heat diffuses quickly, whereas a high $P_r$ usually indicates that convective heat transfer is a dominant mechanism of heat transfer, and heat diffuses less quickly.

It can be seen from FIG. 2 that in multiphase flow, a high density fluid is likely to be adjacent to the lower temperature sensors 7, 8 whereas a lower density fluid will be flowing adjacent to the higher temperature sensors 4, 5. This type of flow is termed stratified flow. The invention can be applied to other types of flow, but stratified flow is used as an example.

Figure 4:
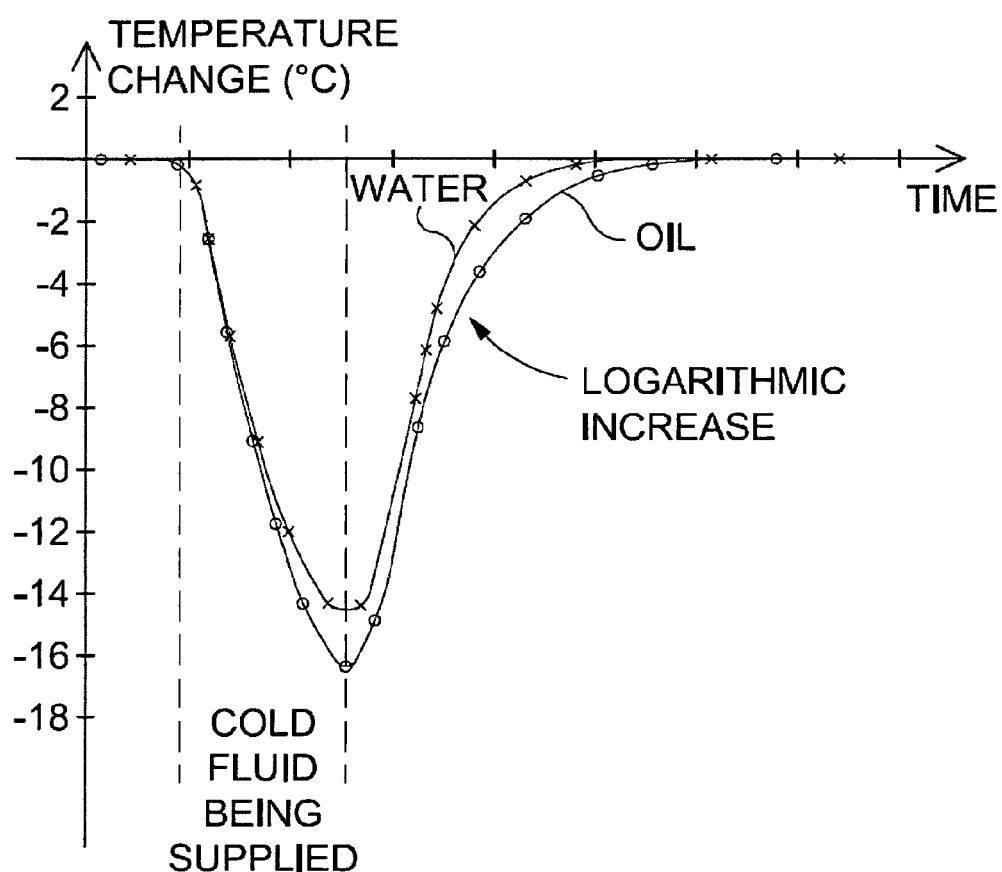
FIG. 4 is a graph showing an example temperature response to a pulse of cold water supplied to the production equipment for two sensors when measuring stratified multiphase flow.

FIG. 4 shows an example thermal response from temperature sensor 4 and temperature sensor 8 in an example in which the production equipment 1 is transporting oil and water in stratified flow will therefore be different. This may be a representative response for application of cold fluid and cooling of a wall portion for a period of 10-30 seconds. In this example, owing to the differing densities of the two fluids, temperature sensor 4 is adjacent to oil in the production equipment 1, and temperature sensor 8 is adjacent to water in the production equipment 1. The temperature at the sensor 8 adjacent to the water falls more quickly, reaches a lower value, and rises more quickly than the temperature at the sensor 4 adjacent to the oil. This information can be used to assist in characterizing multiphase flow, or at least in determining which phases are present and at what points in the conduit.

In order to improve the quality of the measurements, and improve the signal to noise ratio, a time constant is extracted from the temperature response of each sensor from the change in temperature after the cold pulse. A logarithmic increase in temperature occurs shortly after the minimum temperature has been measured. Rather than measuring the time it takes to reach a certain temperature level, which would only use one temperature measurement point and may in general introduce a great deal of uncertainty (although in specific cases a single measurement value can be sufficient), determining the time constant from the logarithmic increase in temperature uses a large series of points and smoothes out corresponding errors.

If the phases expected in the production equipment are already known (in this case pure oil and pure water with no dispersion) then the flow regime can easily be determined. The time constant can be used to determine one or more parameters of the fluid, such as the type of fluid flowing in proximity to the temperature sensor.

Figure 5:
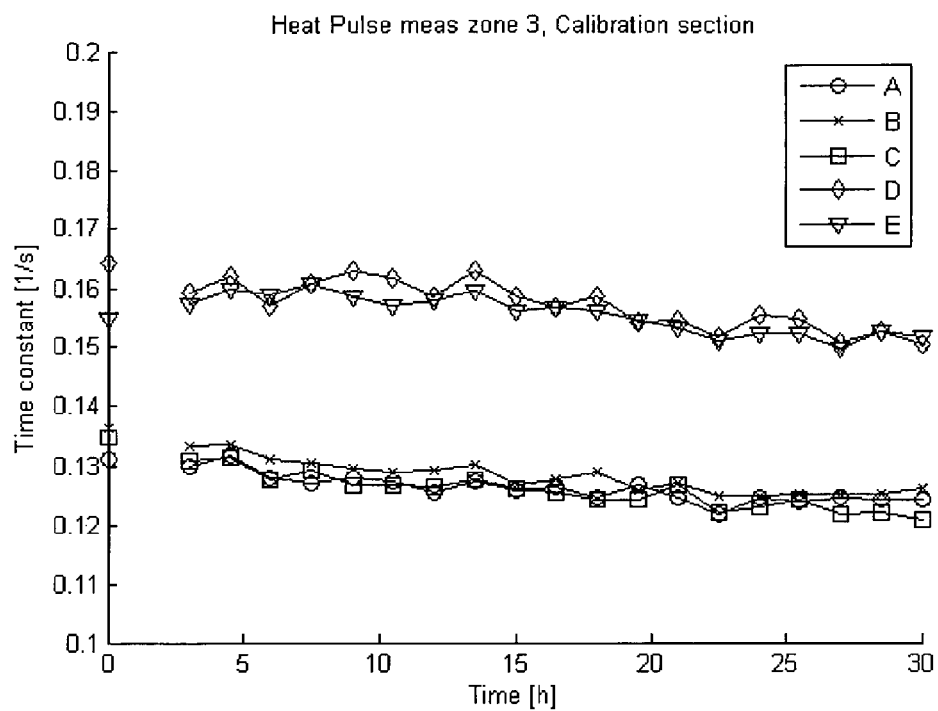
FIG. 5 is a graph showing an example time constant for a plurality of sensors for stratified multiphase flow in a pipeline.

Turning to FIG. 5, an example time constant for each sensor 4, 5, 6, 7, 8 is shown. It can be seen that the time constant over a significant period of time for each temperature sensor 4, 5, 6 is around the same, whereas the time constant for temperature sensors 7 and 8 are similar to each other but different to the time constants of temperature sensors 4, 5 and 6. This clearly indicates a stratified flow with one fluid phase in the production equipment 1 up to at least the level at which temperature sensor 7 is located, and another fluid phase in the production equipment 1 above the level at which temperature sensor 7 is located.

The time constant can be used to characterize fluid flow, as it is affected by both the fluid properties and the flow velocity. For example, the time constant can be measured for single-phase flow (for each of the used fluids in turn) at different flow velocities. This can be used to generate a look-up table of time constants as a function of the type of fluid and the flow velocity. A measurement from a multiphase flow can be subsequently looked-up in the table (the flow velocity has to be measured in parallel) to determine the phase distribution. This may be done manually or using a computer to give an indication of fluid flow.

If a reliable model of fluid flow within the measurement geometry is available, then the heat transfer coefficient can be calculated from the measurement result. The heat transfer coefficient depends on the Prandtl number and the Reynolds number. The Reynolds number is known, and so the Prandtl number can be determined. The Prandtl number can then be compared with the known Prandtl numbers of the expected fluids in the production equipment. Note that the material properties such as the Prandtl number are also dependent on the bulk temperature in the production equipment, so temperature needs to be known (either measured or simulated) and the material parameters need to be adjusted according to the current temperature.

If the phase distribution is not already known, for example, one phase may be a dispersion of oil in water, and another phase may be oil, then the time constant measured at each sensor is compared with a time constant previously measured for a known fluid that the production equipment is likely to contain. The time constant can vary according to the nature of the fluid, the flow rate of the fluid and the temperature of the fluid.

In this way, the characteristics of the fluid in proximity to each of the temperature sensors can be determined and a picture can be built of the location within the production equipment 1 that phases can be found. It will be appreciated that providing more temperature sensors located at different points around the production equipment 1 will result in a more accurate picture of phase distribution in the multiphase fluid flow within the production equipment 1.

Figure 6:
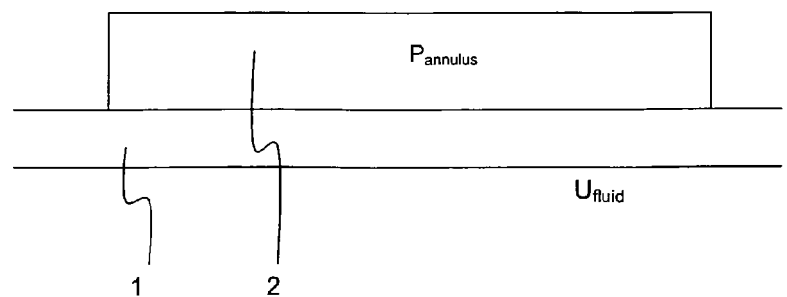
FIG. 6 is a finite element model of the cooling process according to an embodiment of the invention.

In order to get even more information to characterize the multiphase fluid flow, it is possible to calculate the Prandtl number of the fluid using the measured temperature response using a Finite Element Method (FEM) representation of the geometry, as shown in FIG. 6. Comparing the calculated Prandtl number with previously measured Prandtl numbers of the various fluids (e.g. oil/water dispersions at various water cuts) can be used to give an even more detailed picture of the phase distribution.

The simplified FEM model illustrated in FIG. 6 shows the wall of the production equipment 1, and the cooling chamber 2. Fluid flow occurs on the opposite side of the production equipment 1 wall to that of the cooling chamber 2. The cooling chamber 2 in this model is considered to be insulated from ambient temperature, and $U_{fluid}$ may be obtained for oil, water, or a mixture of fluids. Note that FIG. 6 illustrates a very simple geometry, and more complex geometries may be modelled. For example, a layer of wax deposits on the production equipment wall may be modelled.

Figure 7:
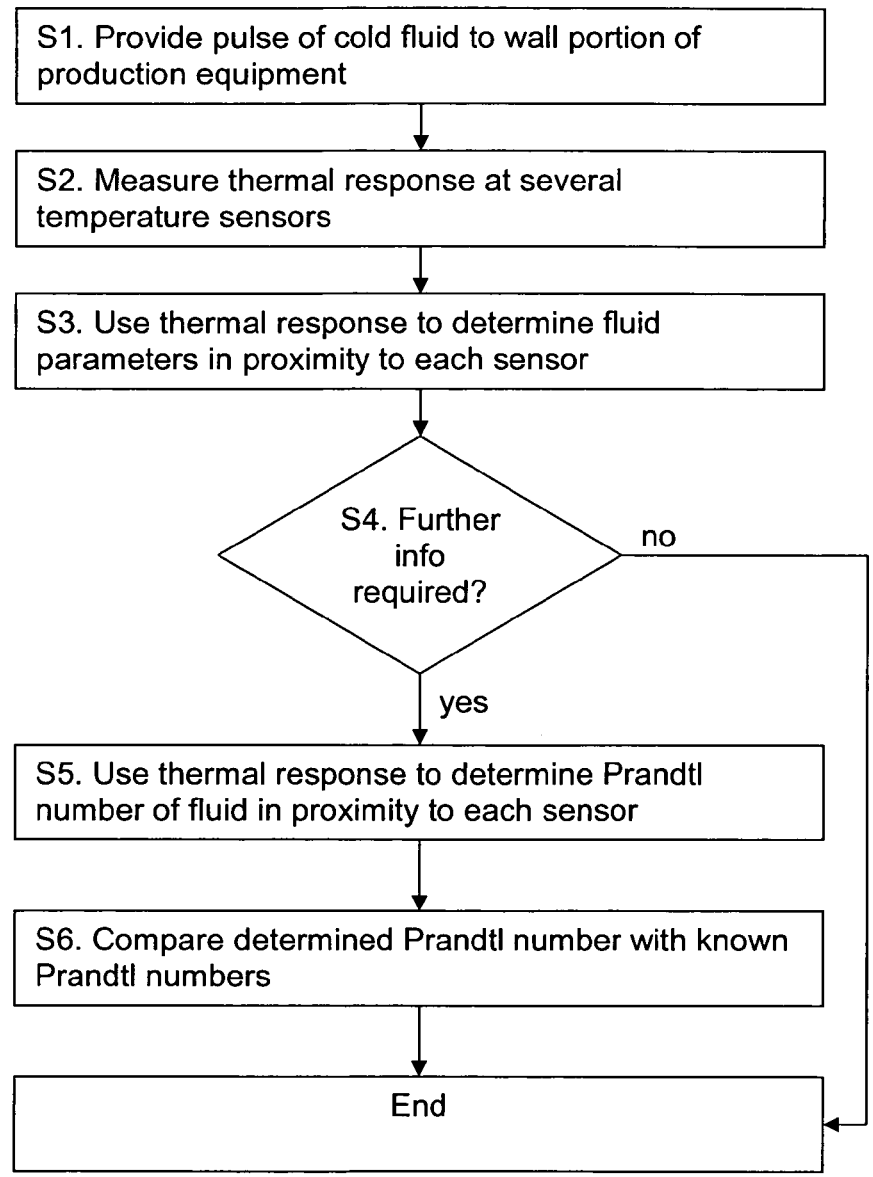
FIG. 7 is a flow diagram showing steps according to an embodiment of the invention.

Turning now to FIG. 7, there is a flow diagram illustrating the steps according to an embodiment of the invention. The following numbering corresponds to that of FIG. 7:

S1. A pulse of cold fluid is applied to a wall of the production equipment carrying multiphase fluid flow.

S2. The thermal response is measured at several temperature sensors disposed in proximity to the production equipment. A time constant is obtained for each sensor using the increase in temperature after a minimum is reached.

S3. The thermal response at each temperature sensor is used to determine fluid parameters, such as the nature of the fluid, in proximity to each temperature sensor.

This may require comparing the thermal response with previously obtained thermal responses for known fluids under known conditions.

S4. If no further information is required, then the process ends.

S5. If further information is required, then the Prandtl number of the fluid in proximity to each temperature sensor is calculated using FEM.

S6. The Prandtl number calculated at each temperature sensor is compared with Prandtl numbers for known fluids.

Figure 8:
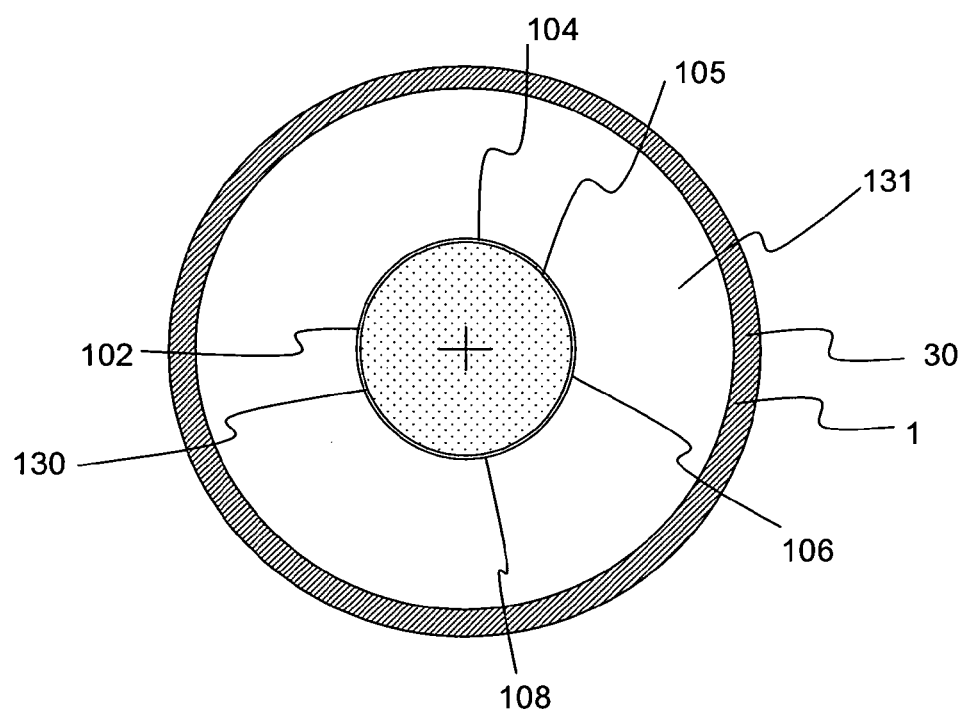
FIG. 8 is an end on cross-sectional view of a separator with an internal cooling chamber according to another embodiment of the invention.

Turning now to FIG. 8, there is shown production equipment 1 with a cooling chamber 102 fitted inside the production equipment 1. The cooling chamber may be removably fitted. In this example, the production equipment is a separator and the cooling chamber 102 is defined by a hollow rod extending into the plane of the page, along a longitudinal axis of the separator. A conduit 131 is defined inside the production equipment, for receiving a multiphase flow therein, between an inner surface of wall 30 of the production equipment and an outer wall surface of wall 130 of the cooling chamber 102. Temperature sensors 104, 105, 106, 108 are disposed adjacent to a wall portion of wall 130 of the cooling chamber around an inner circumference thereof. The temperature sensors are used to measure a thermal response upon subjecting the cooling chamber wall portion to a pulse of cold fluid. The thermal response may for example be a time constant or single measurement of temperature. More specifically, in response to the application of the pulse of cold water, the sensors measure a fall and thereafter a rise in temperature of the wall portion due to the presence of hot fluids inside the conduit, in the same way as in the embodiment described above with reference to FIG. 2 in which the temperature sensors are provided on the wall 30 of the production equipment. The pulse of cold fluid is provided to the wall of the chamber by using a fluid supply apparatus 20, and may be controlled using a computer device 9. In this way, on one side of the wall 131 a conduit is defined, by an outer surface of the wall 130, for carrying the multiphase flow, whilst a pulse of cold fluid is supplied and temperature sensors are provided adjacent to an inner surface of the wall 131 on another, other opposing side of the wall 130. It will be appreciated that the chamber will have inlet and outlets for the supply of fluid (not shown).

A benefit of the arrangement of FIG. 8 is that the wall of the cooling chamber, is thinner than that of the outer wall of the separator, reducing the thermal mass. The thermal response is therefore quicker, reducing the measurement time needed, and allowing a higher measurement frequency. Typically, the wall is made from a metal such as steel.

Figure 9:
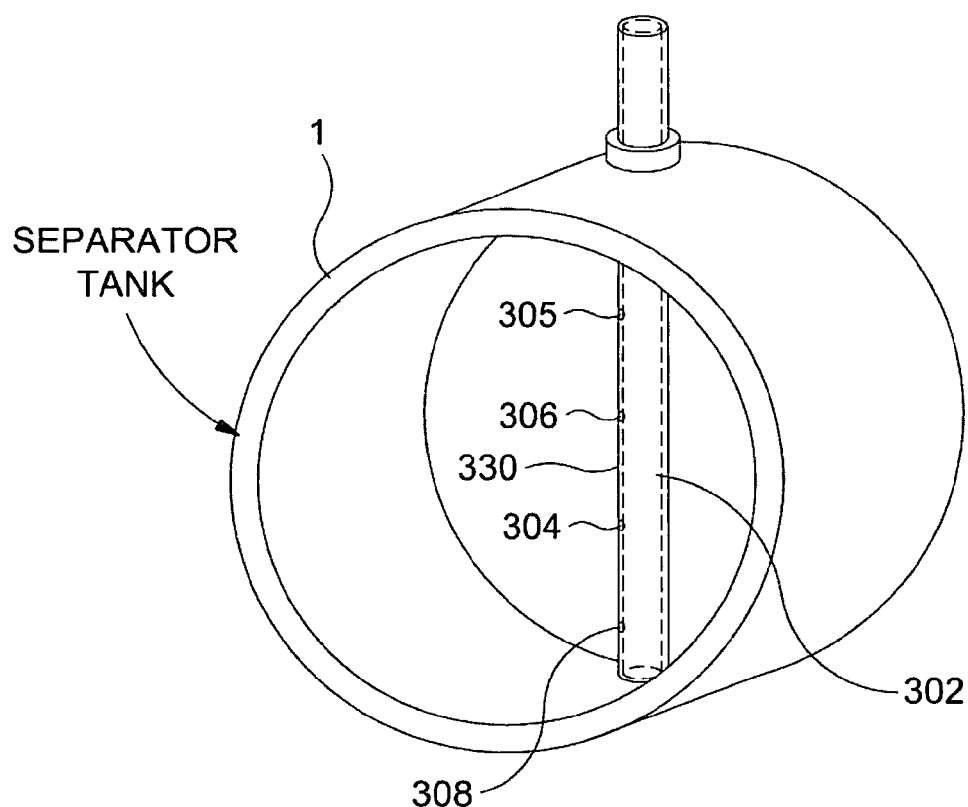
FIG. 9 is perspective representation of a separator with transverse rod defining therein a cooling chamber, according to another embodiment of the invention.

It will be appreciated that an internal rod such as that of FIG. 8 could be arranged inside the production equipment in different orientations, for example vertically or across a longitudinal axis of the production equipment, with temperature sensors in different positions for measuring the thermal response to a cold pulse for characterising a phase distribution. Such an example is shown in FIG. 9. As can be seen, an internally hollow vertical rod extends perpendicularly to the wall of the production equipment 1, into the conduit. The rod defines a cooling chamber 302, and is provided with temperature sensors 304, 305, 306, 308 spaced apart from each other along and coupled to the wall 330 for measuring a temperature response upon applying a pulse of cold fluid to cool the wall 330. It will also be appreciated that in other embodiments, temperature sensors could be placed both around the wall 30 of the production equipment 1 and the wall 130 of the cooling chamber 102, to increase the measurement information and ability to characterise the flow. At the base of the rod inside thereof, an end wall acts to contain the fluid therein and facilitates guiding the supply fluid through the chamber.

Although use of a time constant from the temperature response is used in the embodiments described above, it can nevertheless be possible to derive a phase distribution in other ways. For example, instead of the time constant, a temperature value at a certain point in time after application of the pulse of cold fluid or modelled responses for different fluids to give an indication of the fluid in proximity to the sensor. The known or modelled responses could be stored in a database and looked-up automatically.

In some embodiments, the thickness, presence and/or type of content of the conduit in the form of a waxy layer deposited on the inside of the separator wall may be determined, since the heat transfer coefficient depends upon the thickness of such a layer. In order to determine whether a deposit is present or its thickness, the temperature response may be compared with known or modelled responses for walls with waxy layers of different thicknesses. Alternatively, the temperature response from a sensor where it is unknown whether a waxy deposit is present may be compared with an earlier temperature response for the same sensor, from an earlier application of a pulse of cold fluid differences in responses may be used to infer that a waxy deposit is present. For example, in a multiphase flow comprising an oil/gas stratified flow, it may be assumed that a given point (in this example at the lowest point in a pipe or separator) will always be in oil. All of the changes seen in the temperature response from the temperature sensor at this lowest point will then be due to a build-up or removal of deposit. Another example, in the case of oil/water stratified flow, could similarly use the response from the temperature sensor at the highest point in the pipe/separator to detect a change or presence of a deposit in proximity to the sensor.

Although we have referred above in particular to production equipment in the form of a separator, application of the invention to other types of production equipment can also be advantageous. In particular, it is useful in situations where wax has been deposited because the cooling from applying the pulse of cold fluid keeps the deposit of wax intact, such that the distribution of phases inside the equipment can be kept relatively stable during measurement of the thermal response.

Figure 10:
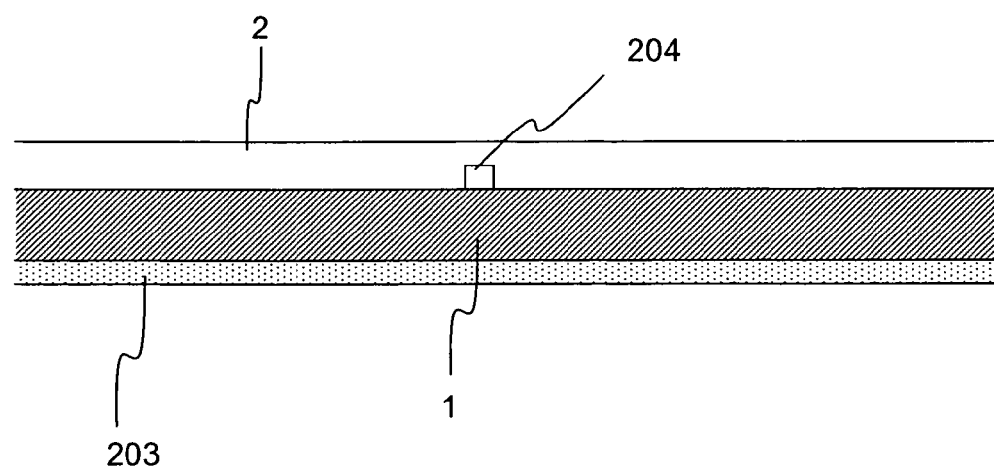
FIG. 10 is a cross-sectional side view of a pipeline section with a cooling chamber showing a layer of waxy deposit, according to another embodiment of the invention.

In some embodiments, a single temperature sensor can be used for determining a multiphase fluid characteristic. Such an embodiment is shown in FIG. 10, where there is provided production equipment 1, in the form of a section of pipe, through which a multiphase flow is transported. This also shows a waxy layer 203 that has been deposited from a multiphase flow on the inside surface of the equipment 1. In the section shown, a cooling chamber 2 is provided around the wall of the production equipment. A single temperature sensor 204 is provided on the wall of the production equipment for measuring a thermal response after subjecting the equipment 1 to a pulse of cold fluid inside the chamber 2. The thermal response can be used to determine a thickness of the deposit or a phase distribution as explained above.

Where a single temperature sensor is used, this provides information on fluid or deposit parameters in proximity to that particular sensor only. This may be sufficient where there is a uniform deposit and/or uniform flow regime.

The invention allows multiphase production equipment such as pipelines and separators to operate more safely and more effectively, as the fluid flow in the production equipment can be monitored and any potential problems can be diagnosed. It is particularly suitable for use with hot equipment, running at elevated temperatures, where cooling of the equipment may provide a particularly convenient, cost effective and safe solution. For example, it may allow temperature tolerances of the production equipment to be relaxed or allow a temperature response to be obtained for characterising the flow with existing equipment and temperature tolerances. The technique is non-intrusive and so does not jeopardize equipment integrity. Furthermore, it can be easily retrofitted to the production equipment at a later date without interrupting existing operations. The invention can therefore be used to monitor multiphase flow within production equipment such as a pipeline or separator. Some types of flow can be destructive or damaging to a pipeline, and monitoring the multiphase flow can highlight any types of flow known to be damaging. This allows remedial action to be taken before flow becomes too damaging.

It should be noted that term "fluid" in relation to a fluid of a multiphase flow, includes fluids in the form of a gas or a liquid or mixed fluids, such as an emulsion or the like, for example an oil-in-water emulsion. It also includes stratified fluids.

Various modifications may be made to the above-described embodiments without departing from the scope of the present invention as defined in the appended claims. For example, while the examples given above apply to a pipeline and separator, the invention may be used to characterize the contents of any type of conduit of production equipment for use in oil and gas production. In addition, it will be appreciated that a cooling chamber as such may not necessarily be required. Any means of cooling the wall portions for a time limited period of time may be suitable.

The invention claimed is:

1. A method of determining contents of a conduit containing at least one fluid, the conduit being at least partially defined by at least one wall portion, the method comprising:
   cooling said wall portion by a cooling chamber;
   after cooling said wall portion, measuring a transient temperature response of the wall portion from each of a plurality of temperature sensors located adjacent to the wall portion;
   determining parameters of the contents of the conduit in proximity to each of the plurality of temperature sensors by using the measured transient temperature responses from each of the plurality of temperature sensors; and
   determining a characteristic of said contents of the conduit using the determined parameters of the contents of the conduit,
   wherein the plurality of temperature sensors are located between the cooling chamber and the wall portion at a position within an axial length of the cooling chamber.

2. The method as claimed in claim 1, wherein the cooling step includes applying a pulse of cold fluid adjacent to the wall portion.

3. The method as claimed in claim 1, including: repeating said cooling step; and measuring the transient temperature response of the wall portion at each of the plurality of temperature sensors after said cooling step and after repeating said cooling step; wherein said determining of a characteristic of the contents is based on both the transient temperature response measured after said cooling step and the transient temperature response measured after repeating said cooling step.

4. The method as claimed in claim 1 including determining a time constant obtained from an increase in the temperature of the wall portion measured at each of the plurality of temperature sensors after a pulse of cold fluid has been provided.

5. The method as claimed in claim 4, wherein the time constant is compared with time constants previously measured for known fluids in order to characterize the contents.

6. The method as claimed in claim 4, wherein the time constant is compared with time constants for known fluids at any of a plurality of different temperatures and flowing at a plurality of different rates.

7. The method as claimed in claim 1, wherein the conduit contains any of: a fluid from a well; a fluid from a multiphase flow; a multiphase fluid; a hydrocarbon production fluid; and a deposit.

8. The method as claimed in claim 1, wherein said characteristic of the contents comprises any of: a distribution of the contents; deposit presence; deposit thickness; and flow regime.

9. The method as claimed in claim 1, further comprising using the measured transient temperature response of the wall portion to determine a Prandtl number of a fluid of the conduit in proximity to at least one temperature sensor of the plurality of temperature sensors.

10. The method as claimed in claim 9, further comprising comparing the determined Prandtl number with Prandtl numbers previously measured for known fluids in order to further characterize the content.

11. The method as claimed in claim 1, wherein the conduit is part of a separator.

12. An apparatus for determining contents of a conduit containing at least one fluid, the conduit being at least partially defined by at least one wall portion, the apparatus comprising:
a plurality of temperature sensors adapted to be fitted adjacent to the wall portion;
a cooling chamber for cooling said wall portion;
a processor configured to:
measure a transient temperature response of the wall portion from each of the plurality of temperature sensors after cooling the wall portion;
determine parameters of said contents in proximity to each of the plurality of temperature sensors by using the measured transient temperature responses from each of the plurality of temperature sensors; and
determine a characteristic of said contents by using the determined parameters of said contents of the conduit,
wherein the plurality of temperature sensors are located between the cooling chamber and the wall portion at a position within an axial length of the cooling chamber.

13. The apparatus as claimed in claim 12, wherein the measured temperature of the wall portion increases after a pulse of cold fluid has been provided and a time constant is obtained from said increase in the temperature of the wall portion measured at each of the plurality of temperature sensors, and the processor is adapted to determine the characteristic of the contents based on the time constant.

14. The apparatus as claimed in claim 12, wherein the processor is further adapted to control operation of a fluid supply of a cold fluid adjacent to the wall portion for cooling the wall portion.

15. The apparatus as claimed in claim 12, wherein the processor further comprises a database, the database storing previously measured thermal responses of known fluids.

16. The apparatus according to claim 12, wherein the processor is further adapted to calculate a Prandtl number of a fluid in proximity to the or each of the plurality of temperature sensors.

17. A computer device for determining contents of a conduit containing at least one fluid, the conduit being at least partially defined by at least one wall portion the computer device comprising:

an in/out device for receiving, from each of a plurality of temperature sensors adjacent to the wall portion, data indicative of a temperature of the contents of the conduit in proximity to each of the plurality of temperature sensors in response to cooling of the wall portion; and a processor arranged to determine a characteristic of the contents based on transient temperature response of the wall portion measured, after cooling the wall portion, at the or each of the plurality of temperature sensors, wherein the plurality of temperature sensors are located between a cooling chamber and the wall portion at a position within an axial length of the cooling chamber.

18. The computer device as claimed in claim 17, wherein the processor is arranged to determine a parameter of the contents of the conduit in proximity to each of the plurality of temperature sensors using the respective measured transient temperature response of the wall portion and to determine a characteristic of the contents of the conduit using the determined fluid parameters.

19. The computer device as claimed in claim 17, wherein the processor is operable to calculate, for each of the plurality of temperature sensors, a time constant obtained from a change in the measured temperature of the wall portion after a pulse of cold fluid has been provided.

20. The computer device as claimed in claim 19, further comprising a database for storing time constants previously measured for known content from a multiphase flow under known conditions, the processor being further arranged to compare each measured time constant with a stored time constant in order to characterize the content.

21. The computer device as claimed in claim 17, wherein the processor is further arranged to determine a Prandtl number of a fluid in proximity to each one of the plurality of temperature sensors.

22. The computer device as claimed in claim 21, further comprising a database for storing Prandtl numbers previously measured for known fluids, the processor being further arranged to compare the determined Prandtl number with the stored Prandtl numbers in order to characterize the contents.

23. The computer device according to claim 17, wherein the processor is further arranged to control a fluid supply of a cold fluid adjacent to the wall portion.

24. A non-transitory computer readable storage medium storing a program, the program comprising computer readable code which, when executed on a computer device, causes the computer device to behave as the computer device as claimed in claim 17.

* * * * *